US006733968B2

(12) United States Patent
Yamamoto et al.

(10) Patent No.: US 6,733,968 B2
(45) Date of Patent: May 11, 2004

(54) MICROARRAY, METHOD FOR PRODUCING THE SAME, AND METHOD FOR CORRECTING INTER-PIN SPOTTING AMOUNT ERROR OF THE SAME

(75) Inventors: Tomoyuki Yamamoto, Kanagawa (JP); Takuro Tamura, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/797,918

(22) Filed: Mar. 1, 2001

(65) Prior Publication Data
US 2001/0034027 A1 Oct. 25, 2001

(30) Foreign Application Priority Data

Mar. 6, 2000 (JP) .......................................... 2000-60787

(51) Int. Cl.[7] .............................. C12Q 1/68; C12M 1/00; C12M 1/36; G01N 15/06
(52) U.S. Cl. ............................ 435/6; 435/7.1; 435/174; 435/283.1; 435/287.2; 435/287.3; 435/288.4; 422/68.1
(58) Field of Search ........................... 435/287.2, 288.4, 435/287.3, 174, 7.11, 283.1; 422/68.1

(56) References Cited

U.S. PATENT DOCUMENTS 6,048,695 A * 4/2000 Bradley et al. ................. 435/6
6,160,618 A * 12/2000 Garner ........................ 356/318
6,251,601 B1 * 6/2001 Bao et al. ....................... 435/6
6,362,004 B1 * 3/2002 Noblett

FOREIGN PATENT DOCUMENTS

JP  11-142408   11/1997
WO  WO 99/22867  10/1998

OTHER PUBLICATIONS

Shalon et al. "A DNA microarray system for analyzing complex DNA samples using two–color fluorescent probe hybridization" Genome Research, Jul. 1996, 6(7): 639–645.*
European Search Report dated May 16, 2003.
Mark Schena, Renu A. Heller, Thomas P. Theriault, Ken Konrad, Eric Lachenmeier and Ronald W. Davis, "Microarrays: Biotechnology's Discovery Platform for Functional Genomics", TIBTECH, Jul. 1998 (vol. 16), pp. 301–306.
Stanley D. Rose, Ph.D., "Application of a Novel Microarraying System in Genomics Research and Drug Discovery", Technical Report, Journal of the Association for Laboratory Automation, vol. 3, No. 3, Jul. 1998, pp. 53–56.

* cited by examiner

Primary Examiner—BJ Forman
(74) Attorney, Agent, or Firm—Reed Smith LLP; Stanley P. Fisher, Esq.; Juan Carlos A. Marquez, Esq.

(57) ABSTRACT

The present invention has an objective of obtaining more accurate data of microarray experiments by correcting an inter-pin spotting amount error caused upon microarray production using a plurality of pins. Upon microarray production, samples are immobilized on a microarray support using all pins as controls for correcting the inter-pin spotting amount errors. After the microarray experiments, luminescent intensities of the samples used as control spots for correcting the inter-pin spotting amount errors are measured and used to obtain correction parameters for the inter-pin spotting amount errors of respective pins. These parameters are used to correct luminescent intensities of other samples.

7 Claims, 7 Drawing Sheets

Microarray information

| ID | Background value | Definition | Pin Type |
|---|---|---|---|
| MA1 | 100 | Sample group from mouse tumor cell | 2x2 |
| MA2 | .... | .... | ... |

501 = ID, 502 = Background value, 503 = Definition, 504 = Pin Type

Fig. 5B

Sample spot information

| ID | MA ID | Sample Name | Definition | Luminescent intensity | X-coordinate of well | Y-coordinate of well |
|---|---|---|---|---|---|---|
| SS 1 | MA1 | Standard Control | Inter-pin spotting amount error correction control | 4500 | 1 | 1 |
| SS 2 | MA1 | Standard Control | Inter-pin spotting amount error correction control | 4600 | 1 | 2 |
| SS 3 | MA1 | Standard Control | Inter-pin spotting amount error correction control | 4400 | 2 | 1 |
| SS 4 | MA1 | Standard Control | Inter-pin spotting amount error correction control | 4700 | 2 | 2 |
| SS 5 | MA1 | Sample1 | Sample 1 from mouse tumor cell | 3000 | 3 | 1 |
| SS 6 | MA1 | Sample2 | Sample 2 from mouse tumor cell | 4600 | 3 | 2 |
| SS 7 | MA1 | Sample3 | Sample 3 from mouse tumor cell | 6500 | 4 | 1 |
| SS 8 | MA1 | Sample4 | Sample 4 from mouse tumor cell | 1000 | 4 | 2 |

| Correction parameter | |
|---|---|
| *Pin1* | |
| 1.01 | |
| *Pin2* | |
| 0.99 | |
| *Pin3* | |
| 1.03 | |
| *Pin4* | |
| 0.97 | |

| Sample | Pin | Measured value | Corrected value |
|---|---|---|---|
| Sample1 | Pin1 | 3000 | 3030 |
| Sample2 | Pin2 | 4600 | 4554 |
| Sample3 | Pin3 | 6500 | 6695 |
| Sample4 | Pin4 | 1000 | 970 |
| Sample5 | Pin1 | 3000 | 3030 |
| Sample6 | Pin2 | 3500 | 3465 |
| Sample7 | Pin3 | 5300 | 5459 |
| Sample8 | Pin4 | 4700 | 4559 |
| Sample9 | Pin1 | 1200 | 1212 |
| Sample10 | Pin2 | 4900 | 5047 |
| Sample11 | Pin3 | 7300 | 7519 |
| Sample12 | Pin4 | 2200 | 2134 |
| Sample13 | Pin1 | 6100 | 6161 |
| Sample14 | Pin2 | 6700 | 6633 |
| Sample15 | Pin3 | 4100 | 4223 |
| Sample16 | Pin4 | 2700 | 2619 |

File  Edit  Help

Open / Print / Exit

Selective display / Sort

Help / About

703 Selective display
- Measured value: ○ Over  ○ Below
- Corrected value: ○ Over  ○ Below 704 Sort
- ○ Sample
- ○ Pin
- ○ Measured value
- ○ Corrected value
- ○ Ascending sort
- ○ Descending sort

MICROARRAY, METHOD FOR PRODUCING THE SAME, AND METHOD FOR CORRECTING INTER-PIN SPOTTING AMOUNT ERROR OF THE SAME

This application claims priority to Japanese Application Serial No. 60787/2000, filed Mar. 6, 2000.

FIELD OF THE INVENTION

The present invention relates to a microarray, a method for producing the same using pins, and a method for correcting inter-pin spotting amount errors of the same.

BACKGROUND OF THE INVENTION

In the fields of molecular biology and biochemistry, biopolymers such as nucleic acids and proteins from organisms are identified and/or fractionated in order to search for useful genes or to diagnose diseases. A hybridization reaction is frequently used as a pretreatment for such process, where a target molecule in a sample is hybridized with a nucleic acid or a protein having a known sequence. For this purpose, microarrays, or so-called biochips or DNA chips, are used on which probes such as DNAs, RNAs or proteins with known sequences are immobilized at predetermined positions.

On a microarray, a plurality of regions called features are defined on which different probes are immobilized. The microarray is placed into a reaction container together with sample DNA or the like to allow the fluorescence-labeled sample DNA to hybridize with the probes immobilized on the respective features of the microarray. Thereafter, the microarray is irradiated with excitation light to measure fluorescent intensity of each feature. Based on the measured fluorescent intensities, the binding levels between the respective probes and the sample DNA are obtained and converted into desired information.

Currently, there are roughly two methods for producing microarrays. One is a method in which oligonucleotides are synthesized on a microarray support, and the other is a method in which samples such as cDNAs are spotted on a microarray support. The latter microarray production method generally uses pins for capturing samples from wells of a well plate storing the samples and immobilizing the samples onto the microarray support. In order to improve speed of producing the microarray, a plurality of pins are used simultaneously. Since many microarray experiments require to measure quantitative differences between the spots, great care should be taken to produce uniform pins and to accurately attach pins to a device not to cause any spotting amount error between the plurality of simultaneously-used pins.

However, as the number of the simultaneously-used pins are increased in order to perform faster microarray production, it becomes more difficult to equalize the spotting amounts of the pins by production of uniform pins and by accurate attachment of the pins to the device (i.e., by hardware means).

In view of the above-described problems, the present invention has objectives of providing a microarray which does not have an influence on measurement results even when there is a difference of spotting amount between pins, a method for producing such microarray, and a method for correcting an inter-pin spotting amount error of a microarray.

SUMMARY OF THE INVENTION

The present invention realizes the above-mentioned objectives by software means. Specifically, a particular sample is spotted using all of the pins to generate control spots (inter-pin error correction control spots) as a part of samples to be immobilized upon microarray production. Luminescent intensities of the inter-pin error correction control spots are measured using a microarray reader, thereby obtaining spotting amount error information. Correction parameters for the inter-pin errors are obtained for respective pins based on the obtained spotting amount errors to correct luminescent intensities of spots on the same microarray measured with the microarray reader, thereby obtaining corrected values for the measured values of the respective spots.

In order to correct the luminescent intensity of each spot, it is necessary to specify which spot has been spotted with which pin. The present invention comprises a database for storing information as to which sample has been taken from which well (coordinate positions) of a well plate storing samples to be immobilized on respective spots upon microarray production, and a program for tracing which pin is actually used for spotting that sample.

A microarray according to the present invention comprises a support on which a plurality of sample spots are arranged in a two-dimensional array, wherein the plurality of sample spots comprise a group of sample spots of identical samples as control spots having a predetermined positional relationship which are used for correcting spotting amount errors among sample spots belonging to other groups of sample spots having the same relative positional relationships as that of the group of control spots.

The sample spots belonging to the groups of sample spots may not be provided on the microarray in an adjacent manner. When the sample spots are to be immobilized on the microarray at a pitch narrower than pin intervals of the pins of the spotting device, the control spots are provided at skipped positions on the microarray.

According to a method of the invention for producing a microarray having a support on which a plurality of sample spots are arranged in a two-dimensional array, an operation is repeated in which a plurality of samples are simultaneously spotted on the support by using a spotting device provided with a plurality of pins, wherein the method comprise a step of simultaneously spotting the same samples on the support with all of the pins of the spotting device. The identical samples simultaneously spotted using all of the pins of the spotting device act as control spots for measuring inter-pin spotting amount errors caused by differences between individual pins of the spotting device.

According to a method of the invention for correcting an inter-pin spotting amount error of a microarray produced by repeating an operation of simultaneously spotting a plurality of samples on a support by using a spotting device provided with a plurality of pins, the method comprises the steps of: simultaneously spotting the same samples as controls on the support with all of the pins of the spotting device, where a plurality of samples are spotted on the support with the spotting device; measuring spotting amounts of the controls spotted with the respective pins of the spotting device to obtain correction parameters for inter-pin spotting amount errors; and correcting a measured value of each sample spot on the support by using the obtained correction parameters for the inter-pin spotting amount errors.

The spotting amounts of the controls using respective pins of a spotting device may be measured after a hybridization reaction with a sample or before the hybridization. When the spotting amounts of the controls are to be measured after the hybridization reaction, for example, luminescent intensities from fluorescence-labeled samples hybridized to the controls may be measured as the spotting amounts of the controls. On the other hand, when the spotting amounts of the controls are to be measured before the hybridization reaction, for example, a predetermined level of fluorescent substance may be contained in the controls so that luminescent intensities from the fluorescent substances can be measured as the spotting amounts of the controls.

According to a method for correcting an inter-pin spotting amount error of the microarray, information for identifying the pins used for immobilizing the samples to respective sample spot locations may be obtained via positional information of wells on a well plate, which store the samples to be transferred to a microplate with the pins.

DETAILED DESCRIPTION OF THE INVENTION

Hereinafter, embodiments of the present invention will be described with reference to the attached drawings. Herein, a spotting device having four pins is exemplified for convenience. However, it is obvious that the present invention is equivalently applicable to microarray production using a spotting device having more than four pins.

Figure 1:
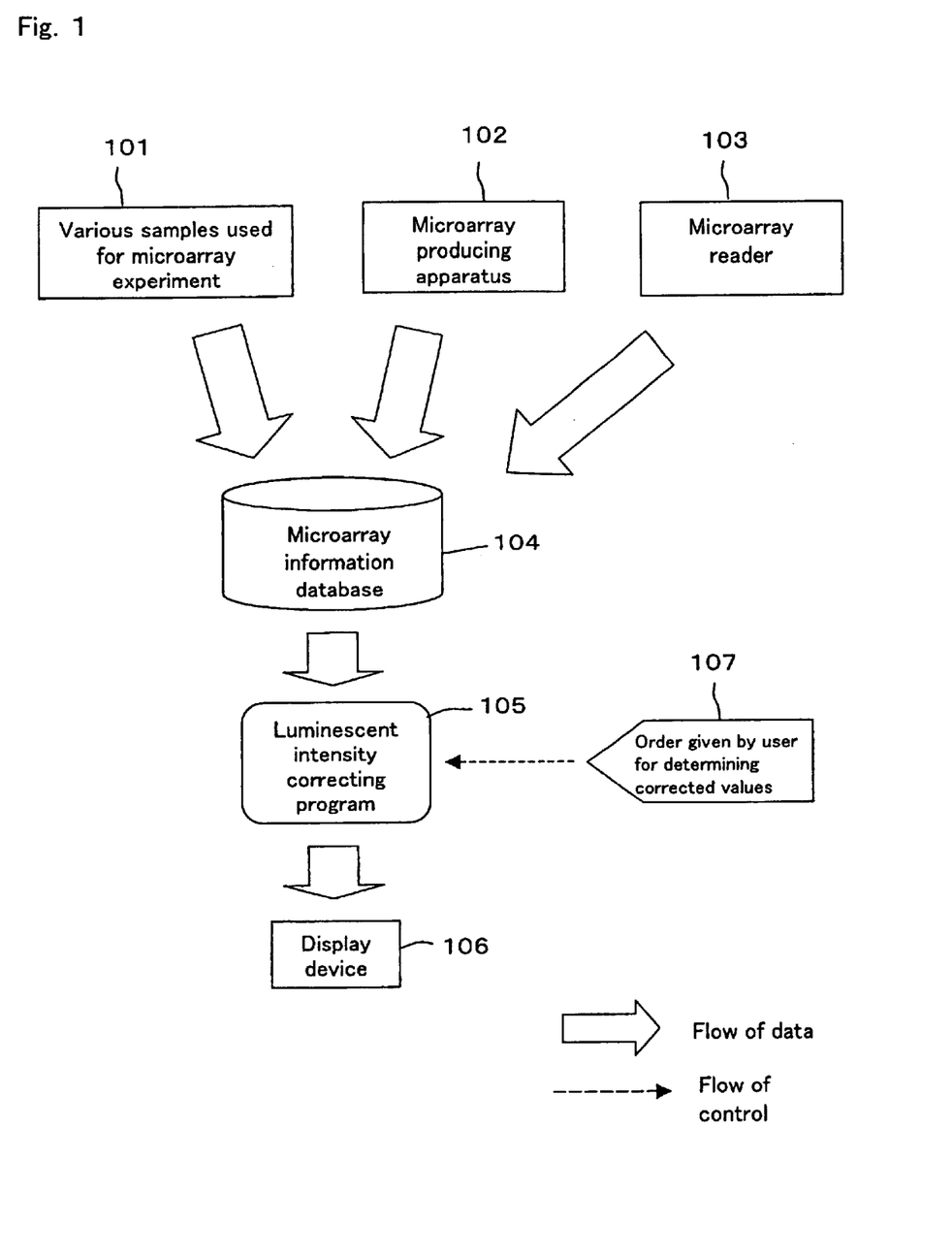
FIG. 1 is a diagram showing an outline of a measurement using a microarray of the invention.

FIG. 1 is a diagram showing an outline of a measurement using a microarray of the invention. For experiments using the microarray, a microarray information database 104 stores sample data, microarray production data and microarray data obtained during the course of preparation of various samples 101, microarray producing apparatus 102 and microarray reader 103. The data in the database 104 is used for identifying the various samples, for storing information as to which sample has been taken from which position of a well plate storing the samples, and for tracing which pin is actually used for spotting that sample. Once an order 107 is given for calculating corrected values of luminescent intensities of respective spots, a luminescent intensity correcting program 105 starts to calculate the corrected value of the luminescent intensity of each spot based on the information acquired from the microarray information database 104, and displays the results on a display device 106. Details of the microarray information database 104, the luminescent intensity correcting program 105 and display on the display device 106 will be described later.

Figure 2:
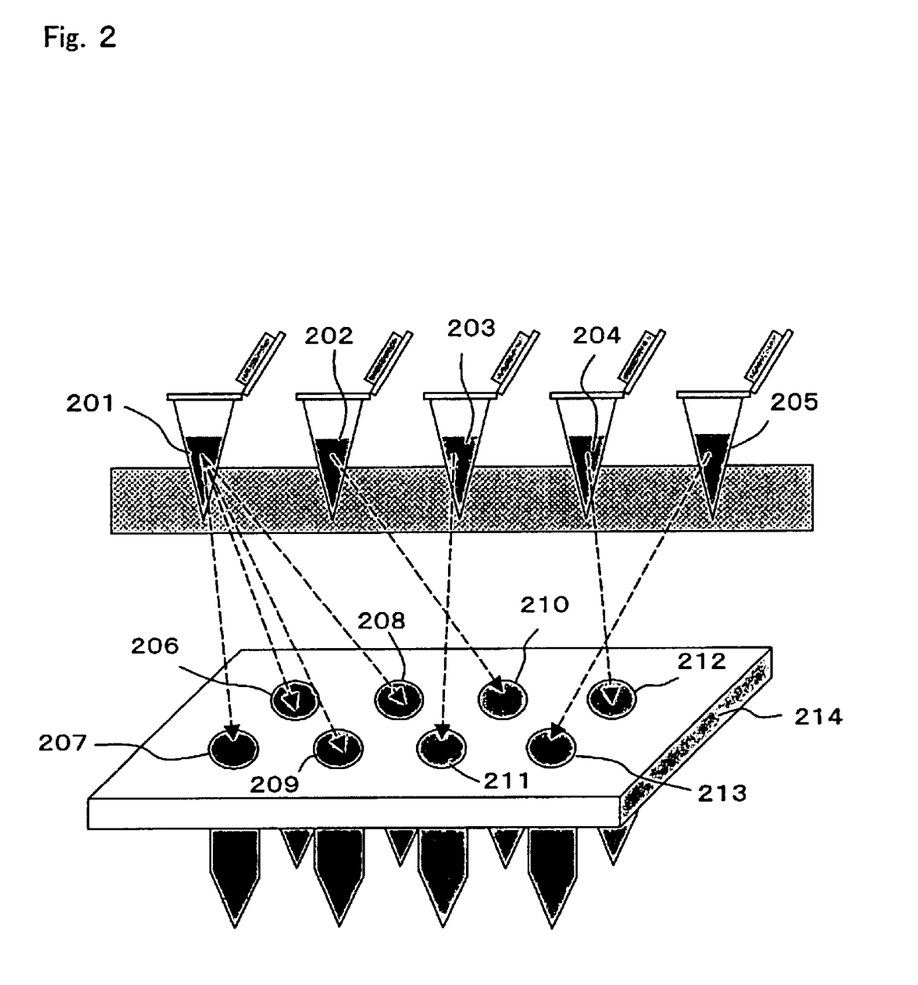
FIG. 2 is a schematic view showing a process for dispensing samples into a well plate.

FIG. 2 is a schematic view showing a process for dispensing samples 201 to 205 prepared for a microarray experiment into a well plate 214. The samples 201 to 205 are samples to be immobilized on a microarray and are stored in respective Eppendorf tubes. The sample 201 is prepared as a control for correcting inter-pin spotting amount errors. The samples 202 to 205 are Samples 1 to Sample 4 as subjects of a test using the microarray. The sample 201 as a control for correcting the inter-pin spotting amount errors is necessary for obtaining corrected luminescent intensities of respective spots and is prepared like other samples.

As represented by broken arrows in FIG. 2, the samples 201, 202, 203, 204 and 205 in the Eppendorf tubes are dispensed into wells 206 to 209, a well 210, a well 211, a well 212 and a well 213 of a well plate 214, respectively. The sample 201 (as the control for correcting the inter-pin spotting amount errors) needs to be dispensed into wells which are at positions where all of the plurality of pins of the spotting device used for immobilization on the microarray are simultaneously accessible to the samples.

At this point, information of the samples 202 to 205, information as to which sample has been dispensed into which well on the well plate 214 and the like can be obtained. The obtained information is stored in the microarray information database 104 as sample spot information.

Figure 3A:
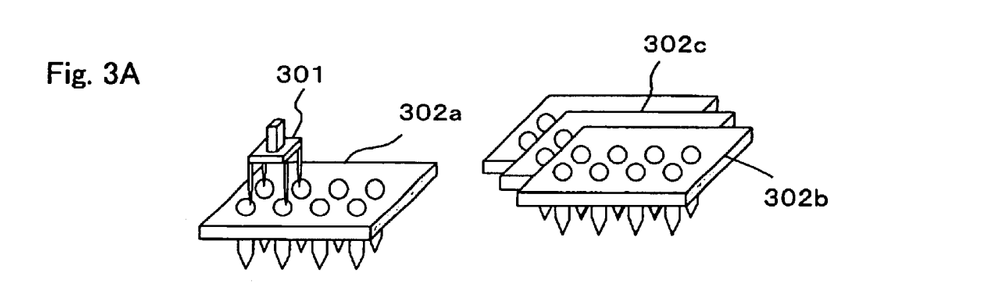
FIGS. 3A and 3B are schematic views illustrating a process of producing a microarray by using a spotting device having a plurality of pins.
Figure 3B:
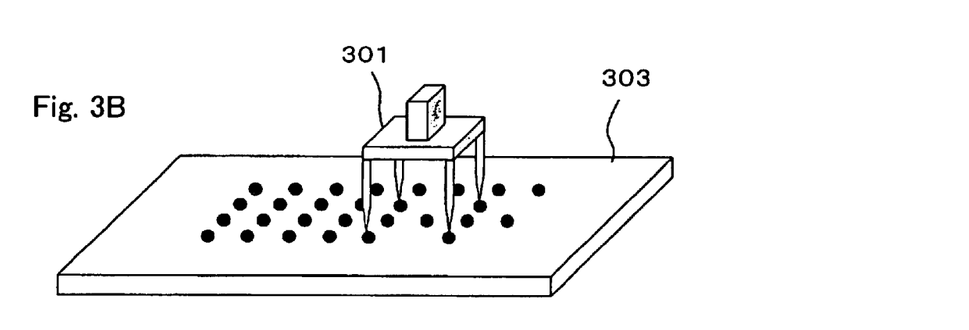

FIGS. 3A and 3B are schematic views illustrating a process of immobilizing samples from the respective wells of the well plate onto the microarray by using the spotting device having four pins. The spotting device 301 has four pins that are capable of simultaneously capturing four kinds of samples from the well plates 302a, 302b . . . . Accordingly, four spots can be spotted on the microarray support 303 at the same time by a single spotting operation. As shown in FIG. 3A, tips of the four pins of the spotting device 301 are immersed into wells of the well plate 302a containing the samples. Then, as shown in FIG. 3B, the tips of the pins of the spotting device 301 capturing the samples make contact with the microarray 303 at designated coordinate positions, whereby the samples on the tips of the pins transfer to the microplate to be immobilized thereon and form sample spots.

At this point, information of the pins or the like used for microarray production is stored in the microarray information database 104 as microarray information. Herein, the alignment between the positions of the samples on the well plates 302a, 302b . . . and the positions on the microarray 303 will not specifically be mentioned since the operations with the pins for immobilizing samples may vary depending on a microarray producing apparatus. However, the alignment here is made suitable.

Figure 4:
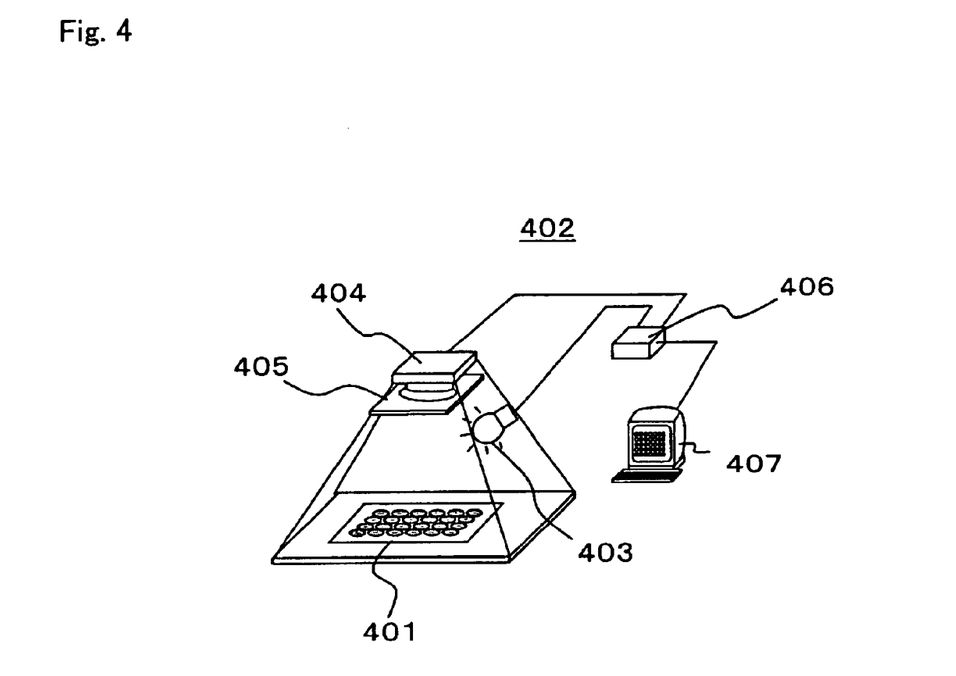
FIG. 4 is a schematic view of a microarray reader.

FIG. 4 is a schematic view showing a process of reading luminescent intensities of respective spots on a produced microarray 401 and a background luminescent intensity of the microarray 401 itself by using a microarray reader 402.

First, a fluorescence-labeled sample is hybridized with samples immobilized on the microarray according to a known method. Thereafter, the microarray 401 is placed beneath the reader 402 to be irradiated with excitation light from a excitation light source 403. Luminescence from fluorescence-labels are read with a two-dimensional optical sensor 404. An optical filter 405 which does not allow passage of the excitation light from the lamp 403 but permits passage of the luminescence from the fluorescence labels is arranged on an optical path of the two-dimensional optical sensor 404. Data of read luminescent intensities of spots and information of the background value between the spots are sent to a computer 407 via a controller 406. Information of luminescent intensity of each spot obtained by reading the microarray information with the microarray reader 402 and information of the background value of the microarray is stored in the microarray information database 104 as sample spot information and microarray information, respectively.

Figure 5A:
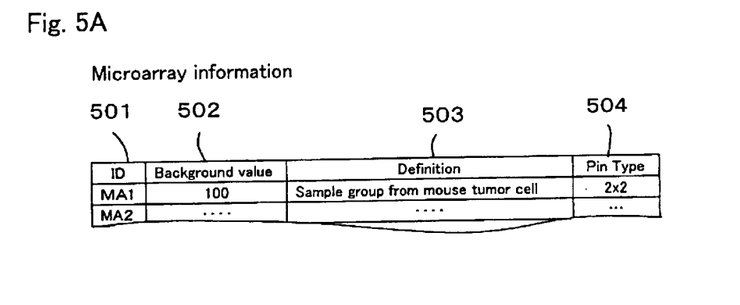
FIGS. 5A and 5B are tables showing an exemplary structure and exemplary data of a microarray information database.
Figure 5B:
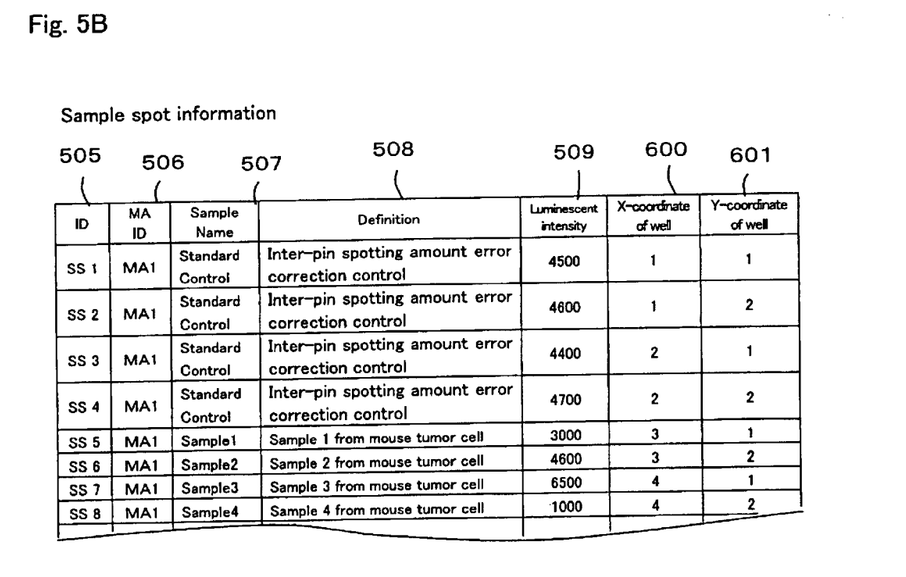

FIGS. 5A and 5B are tables showing an exemplary structure of the microarray information database 104. The table shown in FIG. 5A shows exemplary records of information relative to microarrays, and includes fields such as microarray IDs 501, background values 502 of the microarrays, definitions 503 of the microarrays and types of pins 504 used for microarray production. The table shown in FIG. 5B shows exemplary records of information relative to spots immobilized on the microarray, and includes fields such as spot IDs 505, pointers to the microarray information (microarray IDs) 506, sample names 507, definition information 508, luminescent intensities 509 and positional information 600 and 601 of wells on the well plate.

Based on these data, a pin used for immobilizing a sample on each spot location is specified from a plurality of pins (herein, four pins) of a single spotting device 301 to obtain a correction parameter for an inter-pin spotting amount error for the pin. The obtained correction parameters for the inter-pin spotting amount errors are used to calculate a corrected value of the luminescent intensity of each spot, which will be described below.

Figure 6:
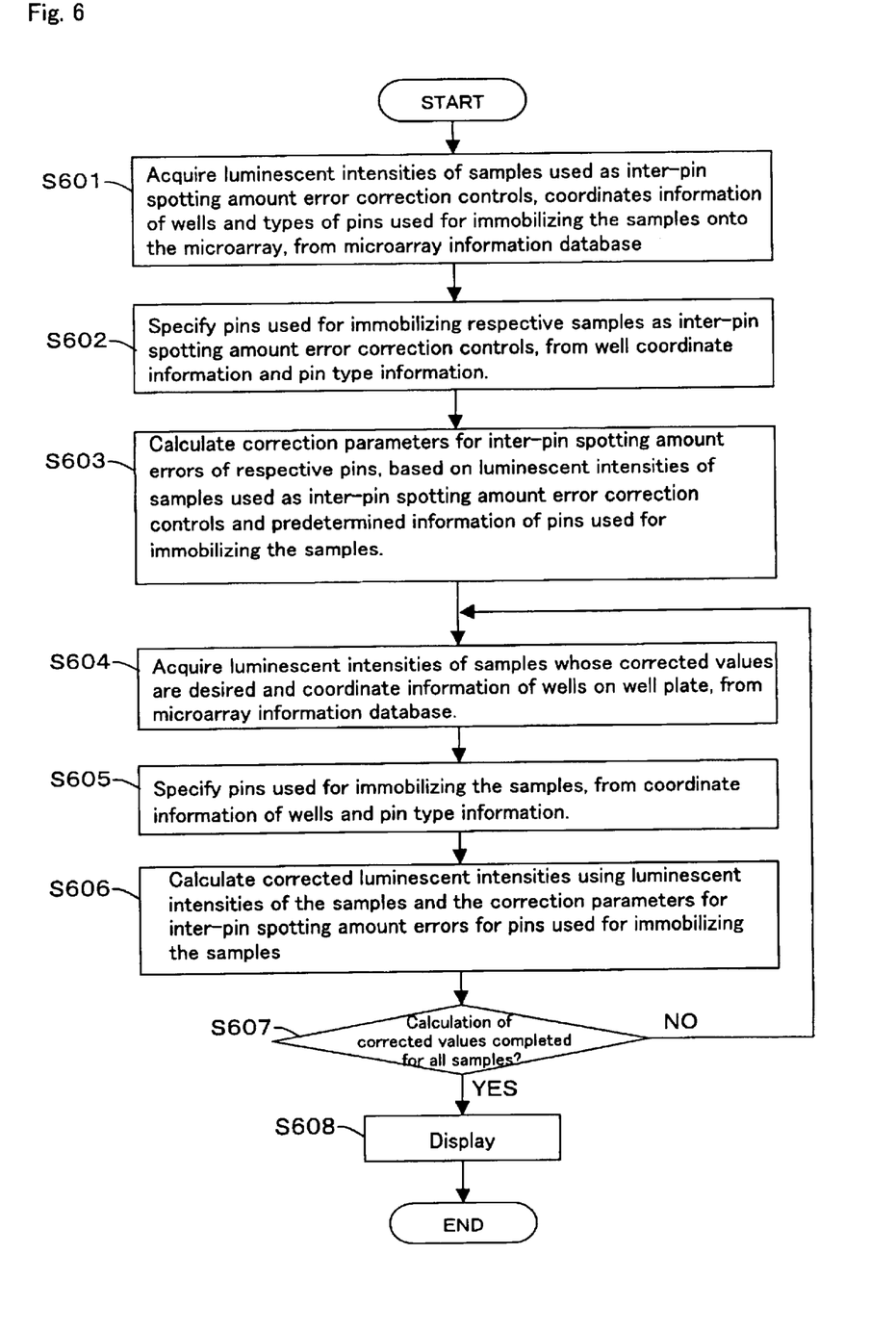
FIG. 6 is a flowchart showing an outline of an operation by a luminescent intensity correcting program.

FIG. 6 is a flowchart showing an outline of an operation by the luminescent intensity correcting program 105 used for calculating a corrected value of the luminescent intensity of each spot. Once the program starts, first samples used as inter-pin spotting amount error correction controls are specified. Information of these samples such as luminescent intensities thereof, well coordinates information thereof and a type of pins used for immobilizing the samples onto the microarray is acquired from the microarray information database 104 (S601). In this example, it can be found from the sample spot information shown in FIG. 5B, that four spots designated spot IDs SS1 to SS4 are derived from the control samples, that the luminescent intensities of these control samples are 4500, 4600, 4400 and 4700, respectively, and that X-Y coordinates of wells containing the respective control samples are (1, 1), (1, 2), (2, 1) and (2, 2), respectively. Further information can be obtained from the microarray information shown in FIG. 5A that the pin type of the microarray designated microarray ID MA1 is 2×2 and that the background value is 100.

Next, from the coordinates information of the wells and pin type information, pins used for immobilizing the respective samples as the controls for correcting the inter-pin spotting amount errors are specified as a set of pin specifying variables (A, B) as calculated by the following [Equation 1] and [Equation 2] (S602).

$$X = \frac{X - \text{coordinate of the well}}{\text{Number of pins along } x\text{-axis}}$$ [Equation 1]

$$Y = \frac{Y - \text{coordinate of the well}}{\text{Number of pins along } y\text{-axis}}$$

X': An integer of X, where the first place of decimal is counted as a whole number when not 0.

Y': An integer of Y, where the first place of decimal is counted as a whole number when not 0.

Pin specifying variable A=x-coordinate of the well−(X'−1)×number of pins along x-axis Pin specifying variable B=y-coordinate of the well−(Y'−1)×number of pins along y-axis [Equation 2]

The above-mentioned [Equation 1] and [Equation 2] are used for determining the pin specifying variables indicating one of the plurality of pins of the spotting device 301, which is used for immobilizing a particular sample onto the microarray. A group of wells storing samples that are captured with the plurality of pins at a time is considered as a single block. [Equation 1] determines a block that meets at the x- and y-coordinates, to which a particular well belong. [Equation 2] gives x-y coordinates of the particular well within the block to which it belongs by subtracting the blocks at the left of and above the block determined by [Equation 1]. Since a single block is a group of wells of samples that are captured with the pins at a time, the obtained coordinates correspond to x-y coordinates of the pin used for the particular well. By using the obtained x- and y-coordinates as pin specifying variables, the pin used for immobilizing the sample in the particular well on the microarray can be specified. In the case of arrangement shown in FIG. 3, pin variables (A, B) determined by above [Equation 1] and [Equation 2] will result in four coordinate sets {(1, 1), (2, 1), (1, 2), (2, 2)}.

Next, correction parameters C.P. (A, B) for inter-pin spotting amount errors of the plurality of pins (A, B) of the spotting device 301 are determined. For this purpose, the above-mentioned pin specifying variables of the respective pins, luminescent intensities of samples used as inter-pin spotting amount error correction controls, and the background value BG of the microarray are used (S603).

A correction parameter C.P. (A, B) for inter-pin spotting amount error of a particular pin specified by pin specifying variables (A, B) is determined by the following [Equation 3].

$$C.P.(A, B) = \frac{\text{Average value of luminescent intensities of controls}}{\text{Luminescent intensity of control of pin } (A, B) - BG}$$ [Equation 3]

The average value of the luminescent intensities of the controls as the dividend of [Equation 3] is obtained by dividing the sum of the luminescent intensities of all controls by the number of the controls, and subtracting the background value BG of the microarray from the obtained value. Thus, correction parameters C.P. (1, 1), C.P. (2, 1), C.P. (1, 2) and C.P. (2, 2) are obtained for the inter-pin spotting amount errors of the four pins.

Then, a luminescent intensity of a particular sample whose corrected value is desired and coordinates information of its well on the well plate are obtained from the microarray information database 104 (S604).

Based on the coordinates information of the well of the particular sample and pin type information, pin specifying variables (A, B) are determined by above [Equation 1] and [Equation 2] for the pin used for spotting that particular sample. Sample spots having identical pin specifying values are samples spotted with the same pin. Thus, the pin used for spotting the particular sample on the microarray can be specified (S605).

By using the inter-pin spotting amount error correction parameter C.P (A, B) of the pin used for immobilizing the sample, the corrected luminescent intensity (corrected value) is calculated by the following [Equation 4] (S606).

Corrected value=C.P. (A, B)×(luminescent intensity of the sample−BG) [Equation 4]

When corrected intensity values of more than one sample need to be calculated, Steps 604 to 607 are repeated until calculation of the corrected values for all of the desired samples are judged to be completed at Step 607. Finally, the determined corrected values of the luminescent intensities of respective samples are displayed on a screen (S608).

Figure 7A:
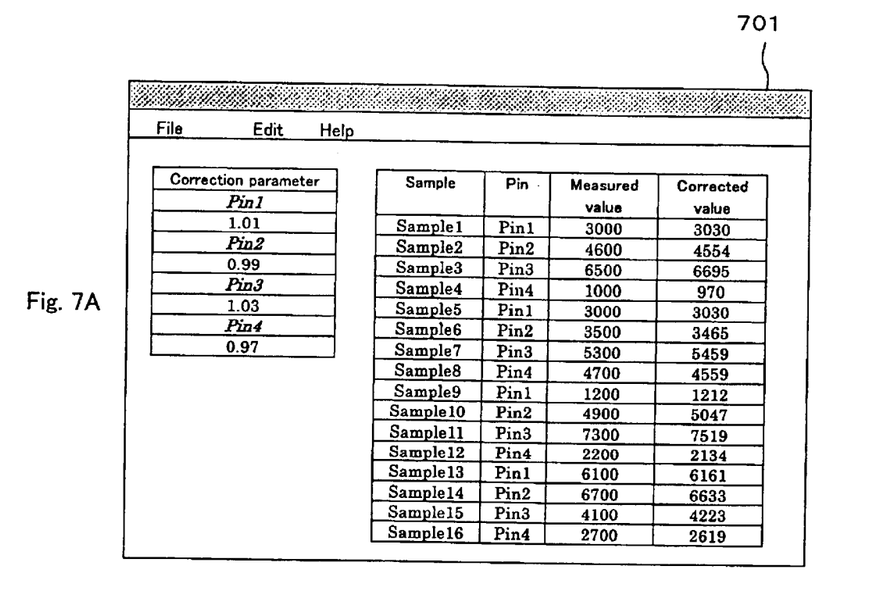
FIGS. 7A to 7C are views showing exemplary screens for displaying corrected values of luminescent intensities.
Figure 7B:
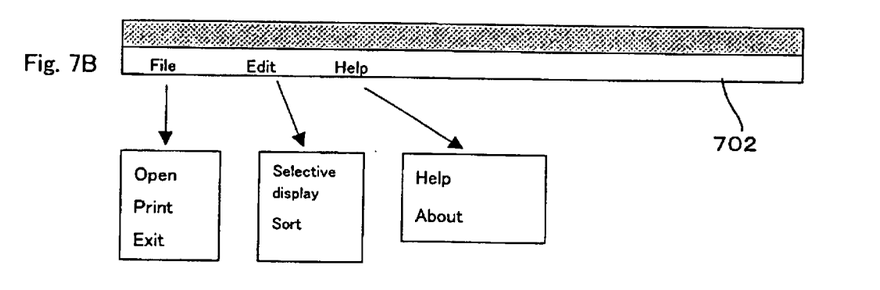
Figure 7C:
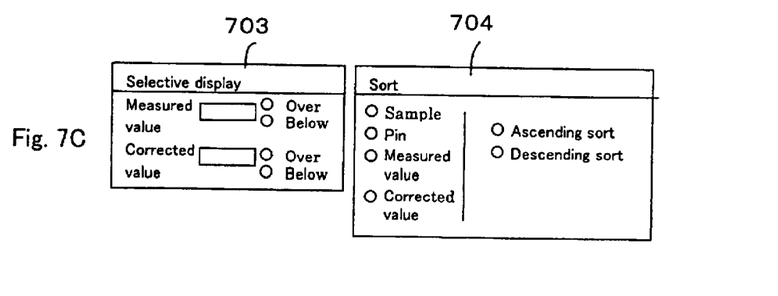

FIGS. 7A to 7C are views showing exemplary screens. As shown in FIG. 7A, a screen 701 for displaying corrected luminescent intensities includes information such as sample names, pins used for immobilizing the respective samples, measured luminescent intensities and corrected luminescent intensities of the respective samples, and correction parameters for inter-pin spotting amount errors for the respective pins. As shown in FIG. 7B, a command "selective display" or "sort" can be selected from [Edit] menu on a menu bar 702 of the corrected value displaying screen 701 to open a dialog box 703 for selective display or a dialog box 704 for sorting as shown in FIG. 7C. By operation on these dialog boxes, data displayed on the corrected value displaying screen 701 can be processed.

According to the above description, correction parameters C.P. (A, B) for inter-pin spotting amount errors of a microarray are determined after a hybridization reaction of the microarray. However, correction parameters C.P. (A, B) for inter-pin spotting amount errors of a microarray may be determined by measuring control spots already containing a fluorescent substance after sample spotting and before a hybridization reaction.

According to the present invention, luminescent intensity errors caused by spotting amount errors between individual pins upon microarray production can be corrected, thereby obtaining measurement results that are not influenced by the quality of the hardware.

What is claimed is:

1. A microarray comprising a support on which a plurality of groups of sample spots are arranged in a two-dimensional array, wherein the plurality of groups of sample spots consist of a group of control spots formed in a predetermined positional relationship with each other, the control spots each having an identical sample therein and containing inter-group spotting amount errors corresponding to the predetermined positional relationship, and other groups of sample spots, each group of the other groups of sample spots having sample spots formed in the same predetermined positional relationship with each other as said group of control spots and having different samples which are different from each other therein, each group of the other groups of sample spots containing the same group of inter-group spotting amount errors as in said group of control spots.

2. The microarray according to claim 1, wherein the group of control spots or said other groups of sample spots are not positioned adjacently.

3. A method for providing a microarray on a support a plurality of groups of sample spots arranged in a two-dimensional array, wherein plurality of groups of sample spots consist of a group of control spots formed in a predetermined positional relationship with each other, the control spots each having an identical sample therein and containing inter-group spotting amount errors corresponding to the predetermined positional relationship, and other groups of sample spots, each group of the other groups of sample spots having sample spots formed in the same predetermined positional relationship with each other as said group of control spots and having different samples which are different from each other therein, each group of the other groups of sample spots containing the same group of inter-group spotting amount errors as in said group of control spots, comprising the steps of:

(a) providing a spotting means consisting of a plurality of pins in the predetermined positional relationship as said group of control spots;

(b) having the plurality of pins of the spotting means capture the identical sample;

(c) simultaneously spotting the identical sample captured by the pins of the spotting means into the control spots to provide said control spots containing said inter-group spotting amount errors;

(d) having the plurality of pins of the spotting means capture different samples; and (e) simultaneously spotting the different samples captured by the plurality of pins of the spotting means to provide said other sample spots containing said inter-group spotting amount errors.

4. The method of claim 3, wherein the spotting means has at least four pins.

5. An apparatus comprising:

(a) a microarray comprising a support on which a plurality of groups of sample spots are arranged in a two-dimensional array, wherein plurality of groups of sample spots consist of a group of control spots formed in a predetermined positional relationship with each other, said control spots each having an identical sample therein and containing inter-group spotting amount errors corresponding to the predetermined positional relationship, and other groups of sample spots, each group of the other groups of sample spots having sample spots formed in the same predetermined positional relationship with each other as said group of control spots and having different samples which are different from each other therein, each group of the other groups of sample spots containing the same group of inter-group spotting amount errors as in said group of control spots;

(b) an excitation light source for irradiating the microarray;

(c) means for detecting luminescence from each of the sample spots of the microarray;

(d) means for calculating a correction parameter used for correcting the inter-group spot amount errors based on the amount of luminescence from the control spots;

(e) means for correcting the amount of luminescence from said each group of other sample spots of the microarray; and (f) spotting means consisting of a plurality of pins in the predetermined positional relationship as said group of control spots.

6. The microarray according to claim 1, wherein the sample spots are spotted by a spotting means with at least four pins.

7. The apparatus according to claim 5, wherein the spotting means has at least four pins.

* * * * *